United States Patent [19]

Hull et al.

[11] Patent Number: 4,954,649
[45] Date of Patent: * Sep. 4, 1990

[54] METHOD FOR PRODUCING CITRATES

[75] Inventors: Ezekiel H. Hull, Greensboro; Edward P. Frappier, Kernersville, both of N.C.

[73] Assignee: Morflex Chemical Company, Inc., Greensboro, N.C.

[*] Notice: The portion of the term of this patent subsequent to Dec. 8, 2004 has been disclaimed.

[21] Appl. No.: 369,127

[22] Filed: Jun. 21, 1989

Related U.S. Application Data

[63] Continuation of Ser. No. 97,801, Sep. 17, 1987, Pat. No. 4,883,905, which is a continuation of Ser. No. 886,463, May 22, 1986, Pat. No. 4,710,532, which is a continuation of Ser. No. 711,284, Mar. 13, 1985, abandoned, which is a continuation-in-part of Ser. No. 619,583, Jun. 11, 1984, abandoned.

[51] Int. Cl.$^5$ .............................................. C07C 67/08
[52] U.S. Cl. .................................... 560/180; 524/309; 524/310; 560/185
[58] Field of Search ................................ 560/180, 185

[56] References Cited

U.S. PATENT DOCUMENTS

| | | | |
|---|---|---|---|
| 3,025,271 | 3/1962 | Borchert | 560/180 |
| 3,056,818 | 10/1962 | Werber | 560/204 |
| 4,007,218 | 2/1977 | Ghanayem et al. | 560/204 |

FOREIGN PATENT DOCUMENTS

| | | |
|---|---|---|
| 1292140 | 5/1965 | Fed. Rep. of Germany . |
| 863792 | 3/1961 | United Kingdom . |
| 886750 | 1/1962 | United Kingdom . |
| 892943 | 4/1962 | United Kingdom . |
| 921482 | 3/1963 | United Kingdom . |
| 923847 | 4/1963 | United Kingdom . |
| 851600 | 10/1966 | United Kingdom . |

OTHER PUBLICATIONS

Citroflex Trade Number For New Candidates (Jan. 1982).
Citrate Ester Development Products (Apr. 1982).
Citrate Ester Development Products (Oct. 1982).
Citrate Ester Development Products (Dec. 1983).

Primary Examiner—Werren B. Lone
Assistant Examiner—Vera C. Clarke

[57] ABSTRACT

Citrate esters are formed utilizing organic titanates as a catalyst allowing excess alcohol to be removed. Four citrate esters have been found which provide advantageous plasticizing properties to PVC compositions which include superior toxicity test results and superior soapy water extraction test results. The four citrate esters are: acetyltri-n-hexyl citrate, n-butyryltri-n-hexyl citrate, acetyltri-n-(hexyl/octyl/decyl) citrate, and acetyltri-n-(octyl/decyl) citrate. Articles formed from the PVC plasticized mixtures are extremely useful in the medical or health care field as they demonstrate a low order of toxicity.

12 Claims, 1 Drawing Sheet

METHOD FOR PRODUCING CITRATES

This is a continuation of application Ser. No. 07/097,801 filed 17 September 1987, now U.S. Pat. No. 4,883,905 which was a continuation of pending patent application Ser. No. 06/866,463 filed 22 May 1986, now U.S. Pat. No. 4,710,532, which was a continuation of application Ser. No. 06/711,294 filed 13 March 1985, now abandoned, which was a continuation-in-part of application Ser. No. 06/619,583 filed 11 June 1984, also now abandoned.

BACKGROUND OF THE INVENTION

1. Field Of The Invention

Citrate esters are useful as plasticizers for polyvinyl chloride (PVC) resins as certain of these esters provide a low order of toxicity when compared to phthalate esters which have been conventionally used. Other advantages have been noted using certain citrate esters as plasticizers in PVC compositions and articles, including improved resistance to soapy water extraction and low temperature and transport properties.

Medical articles formed from PVC compositions utilizing certain citrate esters as plasticizers provide an improved environment for whole blood and blood platelets compared to PVC formulations utilizing conventional plasticizers. Such medical articles may consist of:

1. bags for the storage of whole blood, packed red cells, platelets and plasma;
2. intravenous tubing for the transportation of blood, blood products and crystalloid intravenous fluids;
3. indwelling intravenous and intra-arterial catheters; and
4. tubing - flexible having contact with whole blood as used in:
   (a) renal dialysis devices;
   (b) corpuscular oxygenators as used in open heart surgery;
   (c) membrane oxygenators for pulmonary failures;
   (d) phagocytosis for the collection of platelets and leucocytes for transfusions; and
   (e) intensive plasma exchange devices.

The preparation of the citrate esters has been found to be significantly enhanced by the utilization of certain organic titanate catalysts which allow the excess alcohol to be removed after the esterification step.

2. Description Of The Prior Art And Objectives Of The Invention

Citrate esters commercially produced using citric acid have long been available and have been used as plasticizers for PVC resins. However, the performance of articles produced from the PVC resin compositions whether utilizing citrate esters known to date or conventional phthalate plasticizers have had many inherent disadvantages. For example, medical-grade PVC compositions are used to form blood bags, tubing and a variety of health-related articles and in recent years toxicity has been a major concern for manufacturers of such articles. Recent reports have identified di-2-ethyl-hexyl phthalate (DEHP) or (DOP) and di-2-ethyl-hexyl adipate (DEHA) as hepatocarcinogens in rodents.

In vitro studies have demonstrated significant growth inhibition of human diploid fibroblasts at DEHP concentrations that are found in whole blood stored for 21 days and platelets stored for 24 hours in conventional blood bags. Transfusion studies in monkeys revealed physiological and histological liver abnormalties for up to 26 months after the cessation of transfusions. Patients undergoing kidney dialysis received an amount of DEHP approximately 10 to 20 times that which produced liver damage in the monkeys. DEHP has also been demonstrated to be a peroxisome proliferator and probably a hepatic carcinogen in animals. These results were largely supported by the standard National Cancer Institute National Toxicology Bioassay Program Study in rats and mice.

Industry's attempt at developing alternative PVC plasticizers have been met with limited success. Two of the polymers utilized in a recent comparative study, PVC-TOTM and polyolefin are presently approved for the storage of blood platelets for up to seven days. This is based on both in vivo survival and function studies and their improved gas permeability as compared to PVC-DEHP. The above formulations (PVC-DEHP and polyolefins) and all others attempted to date have not proven suitable for red cell survival studies. The formulations mentioned also show an increase in osmotic fragility of red cells, elevated plasma hemoglobin levels, and red cell potassium levels. This would implicate red cell membrane lesions.

While certain of the phthalates have excellent plasticizing qualities, their suspected carcinogenic nature renders them doubtful candidates for future medical-grade uses. As an alternative, known citric acid esters such as acetyltri-n-butyl and tri-n-butyl citrate were tried as PVC plasticizers in medical-grade applications but it was determined that these compounds were not entirely satisfactory due to their high soapy water extraction percentages and would therefore not be useful in many medical area applications. Also, it has been found that new production techniques had to be devised for the newer citric acid esters which were determined to have suitable toxicity and physical characteristics when used as PVC plasticizers.

It is therefore an objective of the present invention to provide PVC plasticizers which provide superior toxicity test results in biological studies.

It is also an objective of the present invention to provide plasticizers for PVC compositions which can be processed without difficulty using conventional extrusion, calendering, or plastisol techniques.

It is yet another objective of the present invention to provide new citric acid esters namely: acetyltri-n-hexyl citrate, n-butyryltri-n-hexyl citrate, acetyltri-n-(hexyl/octyl/decyl) citrate, and acetyltri-n-(octyl/decyl) citrate which can be used as plasticizers having desirable physical characteristics when imparted into PVC compositions.

It is still another objective of the present invention to provide PVC compositions and formed articles therefrom having superior results in toxicology studies concerning dermal toxicity, oral toxicity and genetic assays.

Another objective of the invention is to provide a medical article and process for making the same such as a blood bag which will provide an improved environment for containing whole blood or blood platelets.

It is also an objective of the present invention to provide a new process for the manufacture of the four new citric acid esters utilizing organic titanates to provide economical and efficient production methods.

Others objectives and advantages of the present invention will be demonstrated to those skilled in the art as set forth in detail below.

SUMMARY OF THE INVENTION

Citrate esters of the formula:

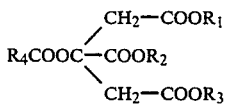

where $R_1$, $R_2$, and $R_3 = CH_3$ to $C_{18}H_{37}$, $R_4 = CH_3$ to $C_7H_{15}$, and more specifically acetyltri-n-hexyl citrate, n-butyryltri-n-hexyl citrate, acetyltri-n-(hexyl/octyl/decyl) citrate, and acetyltri-n-(octyl/decyl) citrate are produced utilizing an organic titanate catalyst and such esters have been found useful as medical-grade plasticizers in PVC compositions. The plasticizers have a low order of toxicity and inpart to PVC the proper balance of physical properties needed in health care and medical-grade uses. The production steps for the citric acid esters include esterification, removal of any excess alcohol and thereafter, alkoxylation. Conventional neutralization and finishing steps are then carried out. The alkoxylation step is carried out at a temperature less than approximately 110° C.

A PVC resin can be combined with one of the above-mentioned citric acid esters, along with suitable stabilizers and lubricants, to form a plasticized PVC which can be extruded, calendered or otherwise processed into suitable articles of manufacture including blood bags, tubing and other products. Articles so made have a low order of toxicity and provide superior extraction properties, particularly in soapy water extraction tests. The soapy water extraction test is a standard test, the results of which closely resemble the results obtained with body fluids such as human blood.

Medical articles formed from PVC compositions employ the above mentioned citrate acid esters demonstrate improved stability characteristics when used for storing whole blood or blood platelets.

DESCRIPTION OF THE PREFERRED EMBODIMENTS

Figure 2:
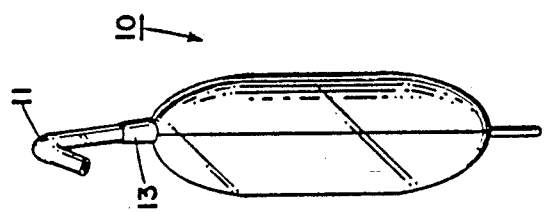
FIG. 2 shows an end view of the blood bag of FIG. 1.

The four preferred forms of the citrate esters are as follows:

1. acetyltri-n-hexyl citrate:

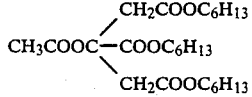

2. n-butyryltri-n-hexyl citrate:

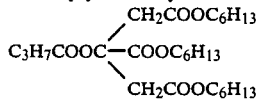

3. acetyltri-n-(hexyl/octyl/decyl) citrate:

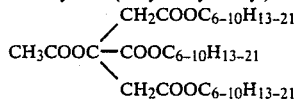

4. acetyltri-n-(octyl/decyl) citrate:

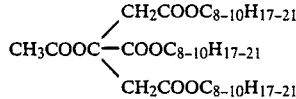

The preferred method of manufacture of the above-identified citrate esters comprises esterification of the proper alcohol (such as n-hexyl alcohol for acetyltri-n-hexyl citrate) with citric acid in the presence of the organic titanate, tetra-n-butyl titanate, removal of any excess n-hexyl alcohol, and then acetylation of the esters produced with acetic anhydride. The acetylation takes place at a temperature of below approximately 110° C. Tetra-n-butyl titanate is preferred since the ester interchange which takes place between the titanate alkyl groups and citrate alkyl groups does not result in the introduction of alkyl groups not normally present in the citrate esters.

The preferred PVC composition comprises blending and milling a medium molecular weight PVC resin with one of the above citrate esters on a two to one ratio, resin to plasticizer, along with stabilizers, lubricants and extenders as required. Articles manufactured from the preferred PVC compositions include blood bags, tubing and other articles for the medical and health care fields.

A medical article such as a blood bag may be made from medical grade components to form a PVC composition having a PVC resin and citrate plasticizer with other ingredients as follows:

|  |  | Parts By Weight |
| --- | --- | --- |
| (a) | PVC resin having an inherent viscosity of .97 | 100 |
| (b) | n-butyryltri-n-hexyl citrate | 50 |
| (c) | epoxidized soybean oil | 10 |
| (d) | stabilizer Ca/Zn | 1 |
| (e) | lubricant (stearic acid) | .1 |

The components are blended by conventional methods and fused. The components are mixed and fused at temperature in the range of 310–360° F. by conventional means such as by use of a blender, followed by pelletizing from an extruder. The pellets are then refused and mixed in an extruder and film, molded articles, etc. are produced from the second extrusion.

Film stock can then be cut and sealed together to form bags for the storage of whole blood, packed red cells, platelets, plasma and intravenous solutions. Such a blood bag generally consists of a transparent pouch having one or more openings for filling, emptying or for tube insertion.

DETAILED DESCRIPTION OF THE INVENTION

Certain citrate esters, namely acetyltri-n-hexyl citrate, n-butyryltri-n-hexyl citrate, acetyltri-n-(hexyl/octyl/decyl) citrate and acetyltri-n-(octyl/decyl) citrate have been found to be particularly useful in medical applications when compounded with PVC resins through conventional plastisol, calendering or extrusion techniques. Such plasticized PVC exhibits good clarity, good low temperature properties, low volatility and low extractability into various media. Also, a low order of acute toxicity has been shown and complete compatibility with medium molecular weight PVC resins make the four named esters unique and valuable. Studies have shown that the four citrate esters are not toxic substances, primary skin irritants or ocular irritants to un-rinsed eyes and oral administration has produced no signs of systemic toxicity and has shown no mortality in fasted mice or rats. Genetic toxicology assays for detecting mutagenic activity at the gene or chromosomal level have shown that these esters do not induce gene mutation in either microbial cells or in mammalian cells in vitro or chromosomal mutation in vivo or in vitro. Studies have also shown that under in vivo conditions, these citrate esters hydrolyze rapidly and completely in concentrations at expected realistic levels of human exposure.

Preparation of the citrate esters are as follows:

EXAMPLE 1: Preparation of acetyltri-n-hexyl citrate 330 lbs. of n-hexyl alcohol, 180 lbs. of citric acid and 1.54 lbs. of tetra-n-butyl titanate and 15 gallons of heptane are charged to a vessel equipped with agitator, thermometer, vapor column, condenser and a decanter set to allow removal of water formed during the reaction while refluxing heptane. The esterification is effected at 140° C. During esterification water is periodically removed from the decanter in order to maintain proper temperature and reaction rates. The esterification is continued until the esterification mixture tests 0.5% maximum acidity calculated as citric acid. Next, the vessel is cooled to 120° C. and any water is removed from the separator and any heptane therein is also removed for future use. The reflux line of the vessel is closed and pressure on the system is reduced slowly. The kettle is heated again to 140° C. and steam is introduced to help remove any residual alcohol. This vacuum steam stripping is continued until alcohol cannot be detected by conventional laboratory tests. When no more alcohol can be found, the steam is discontinued and the temperature is reduced to 100° C. and the vacuum is broken with nitrogen gas.

Next, 0.4 lb. concentrated sulfuric acid ($H_2SO_4$) is charged into the vessel after which it is sealed and approximately 107 lbs. of acetic anhydride (in a determined molar amount) are added at a slow rate so that the temperature does not exceed 110° C. When all the anhydride has been added, agitation of the mix continues for approximately one hour until the acetylation reaction has been completed.

Next, a full vacuum is put on the system and enough heat is added for distillation to proceed at a suitable rate. This step continues until acetic acid is shown to be 5% or less by conventional lab tests whereupon the mixture is cooled to 75° C. for neutralization.

The remaining steps of neutralization, bleaching, washing, etc. are carried out as in conventional esterification processes.

EXAMPLE 2: Preparation of n-butyryltri-n-hexyl citrate:

The vessel used in example 1 is again charged with 330 lbs. of n-hexyl alcohol, 180 lbs. of citric acid and 1.54 lbs. of tetra-n-butyl titanate. Esterification is carried out as in example 1 as is the heptane-alcohol strip. Butyrylization is thereafter done with the addition of 0.4 lbs. of concentrated sulfuric acid and 166 lbs. of n-butyryic anhydride as shown above in the acetylation process. The butyric acid may be removed as shown above or by neutralization.

Examples 1 and 2 produce esters with the following characteristics:

| ANALYTICAL DATA | | |
|---|---|---|
| Property | Acetyltri-n-hexyl Citrate | n-Butyryltri-n-hexyl Citrate |
| Purity wt % | 99 | 99 |
| Color APHA | 50 max. | 50 max. |
| Neut. No. mg KOH/g | 0.2 max. | 0.2 max. |
| Moisture K.F. | 0.25 max. | 0.25 max. |
| S. G. @ 25/25° C. | 1.0045–1.0055 | 0.991–0.995 |
| R. I. @ 25/25° C. | 1.445–1.447 | 1.444–1.448 |
| Viscosity @ 25° C. cps | 25–35 | 25–35 |
| Odor @ 25° C. | Little or none | Little or none |
| Heat Stability (2 Hrs. @ 150° C.) | | |
| Color APHA | 50–60 | 50–60 |
| Neut. No. mg KOH/g | 0.2 max. | 0.2 max. |
| Odor @ 25° C. | Mild | Mild |

In conventional esterification processes, alcohol stripping can be done when acid catalysts such as sulfuric acid, methanesulfonic acid or p-toluenesulfonic acid are used without harmful consequences. However, in the production of the citrate esters of the present invention it has been found that alcohol stripping cannot be done when these acid catalysts are used due to aconitate formation, poor color, yield and other purity problems. The process of the present invention offers a distinct advantage over the conventional process.

Also, other organic titanate catalysts can be used to produce the four (4) esters of this invention such as tetrakis-2-ethylhexyl titanate although superior results have been demonstrated using tetra-n-butyl titanate.

| PREPARATION AND TESTING OF PVC COMPOSITIONS | |
|---|---|
| FORMULATION | PARTS BY WEIGHT |
| Resin (Medium Molecular Weight PVC) | 100 |
| Plasticizer | 50 |
| Stabilizer (Calcium/Zinc) | 2.5 |
| Lubricant (stearic acid) | 0.25 |

The above formulation was blended and milled for 5–10 minutes at 325° to 340° F. The milled stock was pressed (3 min. at 340°–360° F. and 32,000 psi) to 40- and 70-mil sheets, and aged for 48 hours at room temperature for evaluation. All tests were made with samples cut from 70-mil pressed stock except for extraction tests which were obtained on 40-mil samples. The performance data was obtained by accepted ASTM methods with modifications as detailed below Table A.

| | |
|---|---|
| Tensile Strength Ultimate Elongation Modulus (100% elongation) (ASTM D638) | Determined with Instron TT, 1100 series (2 in./min.) using a dumbbell-shaped secimen. Test carried out at 70° ± 5° F. |
| Hardness (ASTM D676) | Determined with Shore Durometer A (10 sec.) at 75° ± 5° F. |
| Torsional Flex ($T_4$ and $T_f$) (ASTM D1043) | Determined with Torsion Flex Tester of Clash and Berg design. $T_4$ is the temperature at which the Modulus of Rigidity is 10,000 psi; $T_f$ is the temperature at which the Modulus of Rigidity is 100,000 psi. |
| Brittle Point (ASTM D746) | Determined by impact method using Scott Tester, Model E. |
| Volatile Loss (A/C) (ASTM D1203) | Determined on specimens 2 inches in diameter heated in activated carbon at 70° C. for 24 hours. Results are expressed as percent of plasticizer lost. |

| | |
|---|---|
| Water extraction (Tap) Soapy Water Extraction | Determined on specimens 2 inches in diameter suspended in appropriate liquid at 60° C. for 24 hours. Results are expressed as percent of plasticizer lost. |
| (1% Ivory Flakes) Oil Extraction (ASTM NO. 3) | |
| Migration Loss (silica) | Determined on specimens 2 inches in diameter heated in silica (100 mesh), at 70° C. for 24 hours. Results are expressed as percent of plasticizer lost. |
| Volatile Loss (air) | Determined by Oven Method (24 hr. at 100° C.) on specimens 2 inches in diameter. Results are expressed as percent of plasticizer lost. |

TABLE A

| | (PLASTICIZER PERFORMANCE DATA) | | | | | | |
|---|---|---|---|---|---|---|---|
| PLASTICIZER | DEHP | DEHA | #1 | #2 | #3 | #4 | #5 |
| HARDNESS, Durometer A, 10 Sec. | 79 | 78 | 78 | 81 | 81 | 87 | 87 |
| TENSILE, psi | 2748 | 1797 | 2862 | 2978 | 2924 | 2743 | 2789 |
| ULTIMATE ELONGATION, % | 395 | 414 | 400 | 390 | 427 | 364 | 374 |
| 100% MODULUS, psi | 1368 | 1092 | 1348 | 1574 | 1362 | 1656 | 1704 |
| $T_4$ (10,000 psi), °C. | −8.4 | −30.8 | −7.6 | −9.1 | −11.9 | −6.9 | −4.0 |
| $T_f$ (100,000 psi), °C. | −38.8 | −66.5 | −35.6 | −41.6 | −48.7 | −53.1 | −59.7 |
| BRITTLE POINT, °C. | −24.5 | −56.5 | −18.5 | −26.0 | −33.5 | −36.8 | −37.8 |
| VOLATILE LOSS, (air), % | 4.8 | 7.1 | 12.1 | 2.6 | 1.7 | .3 | .1 |
| VOLATILE LOSS, (A/C), % | 3.4 | 7.6 | 7.0 | 1.7 | 1.4 | 2.8 | 4.5 |
| WATER EXTRACTION, % | .7 | 1.5 | 1.2 | 1.9 | 1.7 | 1.5 | 3.3 |
| SOAPY WATER EXTRACTION, % | 2.7 | 11.0 | 9.5 | 5.4 | 2.2 | 3.4 | 2.4 |
| OIL EXTRACTION, % | 11.4 | 34.7 | 10.9 | 13.8 | 15.7 | 15.2 | 19.3 |
| SILICA GEL MIGRATION, % | 12.2 | 23.0 | 17.0 | 4.4 | 3.6 | 4.8 | 7.4 |

1 - acetyltri-n-butyl citrate
2 - acetyltri-n-hexyl citrate
3 - n-butyryltri-n-hexyl citrate
4 - acetyltri-n-(hexyl/octyl/decyl) citrate
5 - acetyltri-n-(octyl/decyl) citrate The plasticizer performance data in Table B demonstrates the results of tests with citric esters/expoxidized soybean oil (ESO) blends. ESO is commonly used in conjunction with DEHP at levels in the range of 1-5% based on DEHP as an aid in stabilization. The ratio of 2.5/97.5 ESO/citrate was used as a base point in the studies. Test results on this combination are shown in column 1. A significant improvement in properties, particularly soapy water extraction is noted.

TABLE B

| | (PLASTICIZER PERFORMANCE DATA) | | | | |
|---|---|---|---|---|---|
| PLASTICIZER PERCENTAGES | 2.5 ESO 97.5 #2 | 20 ESO 80 #2 | 40 ESO 60 #2 | 40 ESO 60 #3 | 40 ESO 60 #5 |
| HARDNESS, Durometer A, 10 Sec. | 81 | 80 | 80 | 81 | 85 |
| TENSILE, psi | 2907 | 3010 | 3079 | 3165 | 3097 |
| ULTIMATE ELONGATION, % | 422 | 424 | 420 | 428 | 395 |
| 100% MODULUS, psi | 1415 | 1429 | 1491 | 1514 | 1779 |
| $T_4$ (10,000 psi) °C. | −9.5 | −7.8 | −7.7 | −8.2 | −5.4 |
| $T_4$ (100,000 psi) °C. | −41.8 | −41.3 | −39.3 | −41.8 | −50.3 |
| BRITTLE POINT, °C. | −26.5 | −25.5 | −20.5 | −24.5 | −26.5 |
| VOLATILE LOSS, (Air), % | 2.4 | 2.1 | 1.5 | .8 | .5 |
| VOLATILE LOSS, (A/C), % | 1.3 | 1.6 | 1.4 | .9 | 1.1 |
| WATER EXTRACTION, % | 1.3 | .9 | .6 | .8 | 1.0 |
| SOAPY WATER EXTRACTION, % | 2.9 | 2.9 | 6.4 | 4.8 | 3.8 |
| OIL EXTRACTION, % | 13.0 | 11.6 | 10.1 | 10.0 | 12.9 |
| SILICA GEL MIGRATION, % | 5.7 | 5.3 | 4.7 | 4.0 | 2.5 |

ES0 - Ester/epoxidized Soybean Oil
2 - acetyltri-n-hexyl citrate
3 - n-butyryltri-n-hexyl citrate
5 - acetyltri-n-(octyl/decyl) citrate Since ESO is less expensive than citrates, a reduction in plasticizer cost results if ESO can be substituted for part of the citrates. Results of tests with higher ESO/citrate ratios as shown in columns 2-5 of Table B and a significant improvement in properties up to and perhaps beyond the ratio of 20/80 ESO/citrate ratio as shown.

In vitro evaluation of whole blood and platelets has been undertaken in blood bags prepared with PVC compositions plasticized with di-2-ethylhexyl phthlate (DEPH), or tri-2-ethylhexyl trimellitate (TOTM) and compared to bags utilizing the citrate esters of this invention. The results demonstrate in Table C the improvement in whole blood and platelet characteristics when stored in the PVC blood bags formed with the improved citrate esters. In these studies the decreased amounts of glucose demonstrate the increased consumption by the living blood cells as shown below:

TABLE C

| Plasticizer | Sample | \multicolumn{9}{c}{Glucose mg/dl Days Stored} |

| Plasticizer | Sample | 0 | 7 | | 22 | | 29 | | 36 | |
|---|---|---|---|---|---|---|---|---|---|---|
| DEHP | 1 | 625 | 544 | | 277 | | 260 | | 211 | |
| DEHP | 2 | 625 | 552 | | 285 | | 249 | | 215 | |
| DEPH | 3 | 625 | 552 | | 285 | | 256 | | 221 | |
| Mean ± SEM | | 625 | 549 | ± 2.5 | 282 | ± 2.9 | 254 | ± 3.3 | 215 | ± 3.1 |
| TOTM | 1 | 625 | 559 | | 277 | | 237 | | 191 | |
| TOTM | 2 | 625 | 559 | | 267 | | 232 | | 189 | |
| TOTM | 3 | 625 | 548 | | 270 | | 234 | | 191 | |
| Mean ± SEM | | 625 | 555 | ± 3.8 | 271 | ± 2.9 | 234 | ± 1.4 | 190 | ± 0.4 |
| *Citrate Ester | 1 | 625 | 548 | | 262 | | 220 | | 167 | |
| *Citrate Ester | 2 | 625 | 534 | | 257 | | 217 | | 174 | |
| *Citrate Ester | 3 | 625 | 559 | | 260 | | 222 | | 174 | |
| Mean ± SEM | | 625 | 547 | ± 7.3 | 260 | ± 1.4 | 220 | ± 1.4 | 172 | ± 2.1 |

*n-butyryltri-n-hexyl citrate

As shown in Table D below there was a 47% decrease in platelet count in a PVC bag utilizing a polyolefin polymer, a 38% decrease in a PVC bag plasticized with TOTM and only a 25% decrease in a PVC bag plasticized with the new citrate esters following 7 days of storage.

TABLE D

PLATELET COUNT ($\times 10^9$/ml)

| Blood Bag Polymer | | \multicolumn{4}{c}{Days Stored} |
|---|---|---|---|---|---|
| | | 0 | 1 | 5 | 7 |
| POLYOLEFIN | 1 | 1.41 | 1.33 | 0.78 | 0.76 |
| | 2 | 1.41 | 1.30 | 0.81 | 0.78 |
| PVC-TOTM | 1 | 1.41 | 1.34 | 1.04 | 0.87 |
| | 2 | 1.41 | 1.33 | 0.90 | 0.89 |
| PVC-n-butyryltri-n-hexyl citrate | 1 | 1.41 | 1.34 | 1.27 | 1.13 |
| | 2 | 1.41 | 1.38 | 1.34 | 0.97 |

These test results show a greater platelet survival in the PVC compositions plasticized with the new citrate esters than with the polyolefin or PVC-TOTM compositions.

PVC compositions suitable for extruding tubing, calendering into sheets or film for formation of blood bags and for other medical articles includes a plasticizer of the general formula:

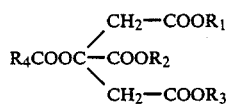

where $R_1$, $R_2$ and $R_3 = CH_3$ to $C_{18}H_{37}$, $R_4 = CH_3$ to $C_7H_{15}$, which is blended into a PVC composition having medical grade or FDA approved components including a medium molecular weight PVC resin as determined by viscosity, with an inherent viscosity range of the PVC resin approximately 0.90 to 1.20; a calcium/zinc stearate stabilizer sold under a number of trademarks and a lubricant such as stearic acid. Additionally, the medical article can be formed from a PVC composition in which an epoxidized soybean oil can be added in the range of 0 to 30 parts by weight. A starting formulation may contain:

| Components | Parts by Weight |
|---|---|
| (a) PVC resin (0.90 to 1.20 inherent viscosity) | 100 |
| (b) Citrate ester | 40 to 70 |
| (c) Epoxidized soybean oil | 0 to 30 |
| (d) Stabilizer | .5 to 5.0 |
| (e) Lubricant | .050 to 0.5 |

Figure 1:
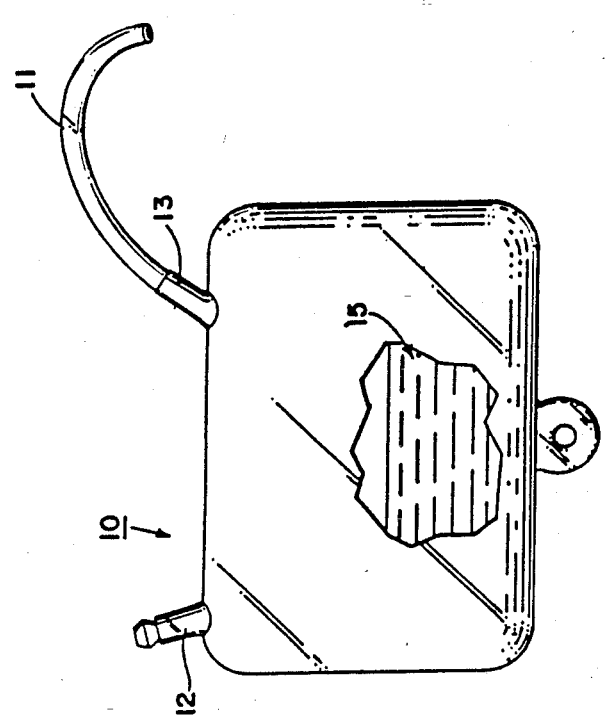
FIG. 1 demonstrates a typical blood bag formed with a citrate plasticizer of the present invention.

A typical blood bag 10 containing platelets 15 with tubing 11 formed with citrate plasticizer of the invention is shown in FIGS. 1 and 2. Spouts 12 and 13 may be used for filling or emptying bag 10 and spout 13 is shown with tubing 11 inserted therein. Bag 10 is formed from a PVC composition of the invention by heat sealing panels cut from PVC sheets of suitable thickness as conventionally produced in the trade. Tubing 11 is made from a PVC composition utilizing a citrate ester of the invention and may be extruded or otherwise shaped to the desired thickness, diameter and length.

Various other PVC compositions can be formulated and the examples and illustrations shown herein are for illustrative purposes and are not intended to limit the scope of the invention.

I claim:

1. A method of producing a 99% pure citrate ester selected from the group consisting of acetyltri-n-butyl citrate, acetyltri-n-hexyl citrate, n-butyryltri-n-hexyl citrate, acetyltri-n-(hexyl/octyl/decyl) citrate and acetyltri-n-(octyl/decyl) citrate, comprising the steps of: heating an alcohol and citric acid in the presence of an organic titanate at a temperature to effect esterification, removing the excess alcohol, alkoxylating the ester while maintaining the temperature below approximately 110° C. until the alkoxylation reaction is complete, cooling and thereafter neutralizing the ester, said ester being 99% pure.

2. The method of claim 1 wherein removing the excess alcohol consists of removing the alcohol by steam stripping.

3. The method of claim 1 wherein said organic titanate is tetra-n-butyl titanate.

4. A method of producing acetyltri-n-butyl citrate comprising the steps of: heating n-butyl alcohol and citric acid in the presence of an organic titanate at a temperature of approximately 140° C. to effect esterification, removing the excess n-butyl alcohol and acetylating the ester by adding acetic anhydride and sulfuric acid while maintaining the temperature below approximately 110° C. until the acetylation reaction is complete.

5. The method of claim 4 wherein said organic titanate is tetra-n-butyl titanate.

6. The method of claim 4 wherein removing the excess alcohol consists of removing the alcohol by steam stripping.

7. A method of producing acetyltri-n-(hexyl/octyl/decyl) citrate comprising the steps of: heating n-(hexyl/octyl/decyl) alcohol and citric acid in the presence of an organic titanate at a temperature of approximately 140° C. to effect esterification, removing the excess n-(hexyl/octyl/decyl) alcohol and acetylating the ester by adding acetic anhydride and sulfuric acid while maintaining the temperature below approximately 110° C. until the acetylation reaction is complete.

8. The method of claim 7 wherein said organic titanate is tetra-n-butyl titanate.

9. The method of claim 7 wherein removing the excess alcohol consists of removing the alcohol by steam stripping.

10. A method of producing acetyltri-n-(octyl/decyl) citrate comprising the steps of: heating n-(octyl/decyl) alcohol and citric acid in the presence of an organic titanate at a temperature of approximately 140° C. to effect esterification, removing the excess n-(octyl/decyl) alcohol and acetylating the ester by adding acetic anhydride and sulfuric acid while maintaining the temperature below approximately 110° C. until the acetylation reaction is complete.

11. The method of claim 10 wherein said organic titanate is tetra-n-butyl titanate.

12. The method of claim 10 wherein removing the excess alcohol consists of removing the alcohol by steam stripping.

* * * * *